(12) United States Patent
Rudie et al.

(10) Patent No.: US 6,490,488 B1
(45) Date of Patent: *Dec. 3, 2002

(54) METHOD OF CONTROLLING THERMAL THERAPY

(75) Inventors: Eric N. Rudie, Maple Grove, MN (US); Jonathan L. Flachman, Robbinsdale, MN (US); James E. Burgett, Maple Grove, MN (US); Thayne R. Larson, Scottsdale, AZ (US)

(73) Assignee: Urologix, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/552,905

(22) Filed: Apr. 20, 2000

Related U.S. Application Data (63) Continuation of application No. 09/210,033, filed on Dec. 11, 1998, now Pat. No. 6,122,551.

(51) Int. Cl.⁷ ............................................... B61N 5/02
(52) U.S. Cl. ..................... 607/102; 607/96; 607/100; 607/101; 607/104; 607/105
(58) Field of Search .............................. 607/96, 100–15

(56) References Cited

U.S. PATENT DOCUMENTS

| | | | |
|---|---|---|---|
| 4,190,053 A | 2/1980 | Sterzer ........................ 128/399 |
| 4,375,220 A | 3/1983 | Matvias ....................... 128/804 |
| 4,601,296 A | 7/1986 | Yerushalmi ................. 128/804 |
| 4,662,383 A | 5/1987 | Sogawa et al. ............. 128/784 |
| 4,676,258 A | 6/1987 | Inokuchi et al. ............ 128/804 |
| 4,813,429 A | 3/1989 | Eshel et al. ................. 128/736 |
| 4,967,765 A | 11/1990 | Turner et al. ............... 128/785 |
| 5,007,437 A | 4/1991 | Sterzer ........................ 428/786 |
| 5,097,829 A | * 3/1992 | Quisenberry ................ 219/490 |
| 5,231,997 A | * 8/1993 | Kikuchi et al. ............. 219/695 |
| 5,234,004 A | 8/1993 | Hascoet et al. ............. 607/116 |
| 5,304,214 A | 4/1994 | DeFord et al. .............. 607/105 |

(List continued on next page.)

FOREIGN PATENT DOCUMENTS

| WO | WO 94/02204 | 2/1994 | ............ A61N/5/02 |
|---|---|---|---|

*Primary Examiner*—Lee Cohen
*Assistant Examiner*—Henry M. Johnson
(74) *Attorney, Agent, or Firm*—Kinney & Lange, P.A.

(57) ABSTRACT

A thermal therapy method includes inserting an applicator including an energy-emitting device into a body cavity such as a urethra adjacent a targeted tissue region such as a prostate, energizing the energy-emitting device, and circulating coolant between the energy-emitting device and a wall of the body cavity. The therapy is controlled by decreasing a temperature of the coolant and continually adjusting coolant temperature based on therapy parameters. The applicator, or selected tissue at a predetermined depth from the wall of the body cavity, is maintained at a temperature corresponding to a predetermined applicator temperature profile by adjusting a power level provided to the energy-emitting device. In one embodiment involving treatment of the prostate, rectal temperature is monitored and, upon sensing a rectal temperature that exceeds a predetermined threshold, the temperature of the coolant is increased to force a reduction in power provided to the energy-emitting device to maintain the applicator at the temperature corresponding to the predetermined applicator temperature profile.

25 Claims, 7 Drawing Sheets

U.S. PATENT DOCUMENTS

| | | | | |
|---|---|---|---|---|
| 5,330,518 A | | 7/1994 | Neilson et al. | 607/101 |
| 5,344,435 A | | 9/1994 | Turner et al. | 607/101 |
| 5,391,197 A | | 2/1995 | Burdette et al. | 607/97 |
| 5,404,881 A | | 4/1995 | Cathaud et al. | 128/653.1 |
| 5,413,588 A | | 5/1995 | Rudie et al. | 607/101 |
| 5,423,811 A | | 6/1995 | Imran et al. | 606/41 |
| 5,433,740 A | | 7/1995 | Yamaguchi | 607/102 |
| 5,464,437 A | | 11/1995 | Reid et al. | 607/101 |
| 5,464,445 A | | 11/1995 | Rudie et al. | 607/101 |
| 5,480,417 A | | 1/1996 | Hascoet et al. | 607/101 |
| 5,496,271 A | | 3/1996 | Burton et al. | 604/54 |
| 5,509,929 A | | 4/1996 | Hascoet et al. | 607/101 |
| 5,520,684 A | | 5/1996 | Imran | 606/41 |
| 5,545,137 A | | 8/1996 | Rudie et al. | 604/96 |
| 5,575,811 A | | 11/1996 | Reid et al. | 607/101 |
| 5,620,480 A | | 4/1997 | Rudie | 607/101 |
| 5,624,382 A | | 4/1997 | Oppelt et al. | 601/2 |
| 5,628,770 A | | 5/1997 | Thome et al. | 607/101 |
| 5,643,335 A | | 7/1997 | Reid et al. | 607/101 |
| 5,676,692 A | | 10/1997 | Sanghvi et al. | 607/97 |
| 5,733,319 A | | 3/1998 | Neilson et al. | 607/105 |
| 5,755,754 A | | 5/1998 | Rudie et al. | 607/101 |
| 5,759,162 A | * | 6/1998 | Oppelt et al. | 600/439 |
| 5,792,070 A | | 8/1998 | Kauphusman et al. | 600/549 |
| 5,800,486 A | | 9/1998 | Thome et al. | 607/105 |
| 5,807,395 A | * | 9/1998 | Mulier et al. | 604/22 |
| 5,843,144 A | | 12/1998 | Rudie et al. | 607/101 |
| 5,861,021 A | | 1/1999 | Rudie et al. | 607/101 |
| 5,899,932 A | | 5/1999 | Dann et al. | 607/113 |
| 5,916,240 A | | 6/1999 | Rudie et al. | 607/101 |
| 5,916,241 A | | 6/1999 | Rudie et al. | 607/101 |
| 5,931,860 A | | 8/1999 | Reid et al. | 607/101 |
| 5,938,692 A | | 8/1999 | Rudie | 607/101 |
| 5,951,546 A | * | 9/1999 | Lorentzen | 606/41 |
| 5,987,360 A | | 11/1999 | McGrath et al. | 607/101 |
| 6,007,571 A | | 12/1999 | Neilson et al. | 607/105 |
| 6,051,018 A | * | 4/2000 | Larsen | 607/101 |
| 6,122,551 A | * | 9/2000 | Rudie et al. | 607/100 |
| 6,216,041 B1 | * | 4/2001 | Tierney et al. | 607/101 |
| 6,302,878 B1 | * | 10/2001 | Daikuzono | 606/15 |

* cited by examiner

METHOD OF CONTROLLING THERMAL THERAPY

CROSS-REFERENCE TO RELATED APPLICATION

This is a continuation of U.S. application Ser. No. 09/210,033 filed Dec. 11, 1998 for "Method of Controlling Thermal Therapy" by E. Rudie, J. Flachman, J. Burgett and T. Larson, now U.S. Pat. No. 6,122,551.

BACKGROUND OF THE INVENTION

The present invention relates to a method for treating tissue. In particular, the present invention relates to a method of controlling thermal therapy of tissue such as the prostate to enhance treatment effectiveness with minimal treatment time.

The prostate gland is a complex, chestnut-shaped organ which encircles the urethra immediately below the bladder. Nearly one third of the prostate tissue anterior to the urethra consists of fibromuscular tissue that is anatomically and functionally related to the urethra and the bladder. The remaining two thirds of the prostate is generally posterior to the urethra and is comprised of glandular tissue. The portion of the urethra extending through the prostate (i.e., the prostatic urethra) includes a proximal segment, which communicates with the bladder, and a distal segment, which extends at an angle relative to the proximal segment by the verumontanum.

Although a relatively small organ, the prostate is the most frequently diseased of all internal organs and is often the site of a common affliction among older men, benign prostatic hyperplasia (BPH), as well as a more serious affliction, cancer. BPH is a nonmalignant, bilateral expansion of prostate tissue occurring mainly in the transition zone of the prostate adjacent to the proximal segment of the prostatic urethra. As this tissue grows in volume, it encroaches on the urethra extending into the region of the bladder neck at the base of the bladder. Left untreated, BPH causes obstruction of the urethra which usually results in increased urinary frequency, urgency, incontinence, nocturia and slow or interrupted urinary stream. BPH may also result in more severe complications, such as urinary tract infection, acute urinary retention, hydronephrosis and uraemia.

Benign prostatic hyperplasia (BPH) may be treated using transurethral thermal therapy as described in further detail in U.S. Pat. No. 5,620,480 entitled METHOD FOR TREATING BENIGN PROSTATIC HYPERPLASIA WITH THERMAL THERAPY and in U.S. Pat. No. 5,575,811 entitled BENIGN PROSTATIC HYPERPLASIA TREATMENT CATHETER WITH URETHRAL COOLING, both of which are hereby incorporated by reference. During transurethral thermal therapy, the transition zone of the prostate is heated to necrose the tumorous tissue that encroaches on the urethra. Transurethral thermal therapy is administered by use of a microwave antenna-containing catheter which includes a multi-lumen shaft. The catheter is positioned in the urethra with the microwave antenna located adjacent to the hyperplastic prostatic tissue. Energization of the microwave antenna causes the antenna to emit electromagnetic energy which heats tissue within the prostate. A cooling fluid is circulated through the catheter to preserve tissue such as the urethral wall between the microwave antenna and the target tissue of the prostate.

The primary goal of transurethral thermal therapy is to necrose prostate tissue while preserving adjacent healthy tissue. It is also preferable to achieve this goal in as short of a time as is possible, consistent with the patient's level of tolerance and comfort. In addition, it is important that the rectum be preserved from unduly high temperatures, since it is susceptible to thermal damage. There is an ongoing need in the art for a method of controlling thermal therapy that reduces treatment time and enhances effectiveness consistent with all of these parameters.

SUMMARY OF THE INVENTION

The present invention is a method of treating tissue with heat from an adjacent body cavity, such as treating a prostate with heat delivered from a urethra. An applicator including an energy-emitting device is inserted into the body cavity adjacent the targeted tissue region. The energy-emitting device is energized, thereby delivering energy to the targeted tissue region, and coolant is circulated between the energy-emitting device and a wall of the body cavity. A temperature of the coolant circulated is continually controlled based on therapy parameters. For example, where the targeted tissue region is the prostate adjacent the urethra, rectal temperature is monitored and, upon sensing a rectal temperature that exceeds a predetermined threshold, coolant temperature is increased. Patient comfort indicators are also an example of therapy parameters upon which continuous control of the coolant temperature may be based. The applicator, or selected tissue at a predetermined depth from the wall of the body cavity, is maintained at a temperature corresponding to a predetermined applicator temperature profile by adjusting a power level provided to the energy-emitting device.

DETAILED DESCRIPTION OF THE PREFERRED EMBODIMENTS

Figure 1:
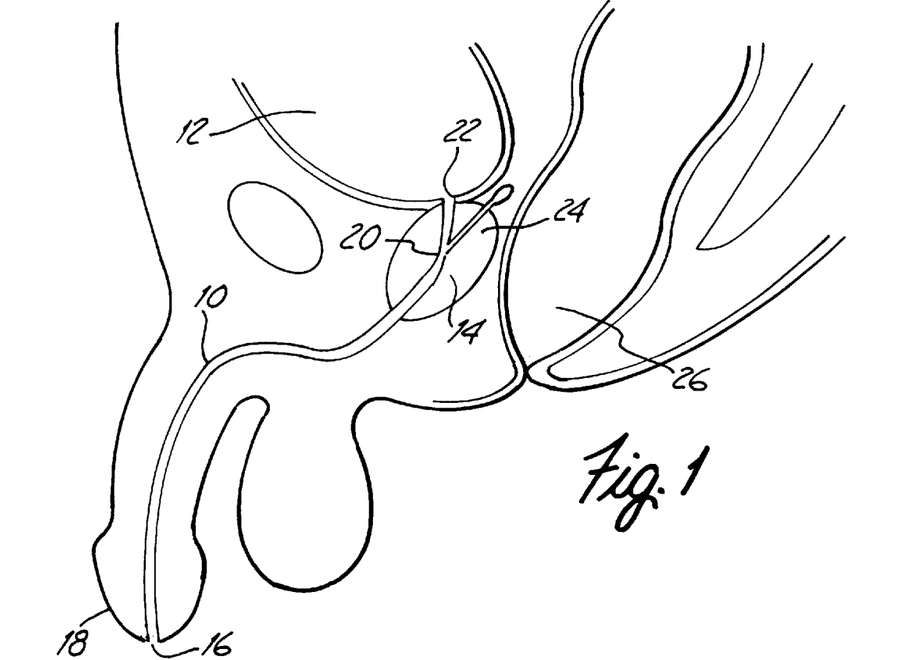
FIG. 1 is a vertical section view of a male pelvic region showing the urinary organs affected by benign prostatic hyperplasia.

FIG. 1 is a vertical sectional view of a male pelvic region showing the effect benign prostatic hyperplasia (BPH) has on the urinary organs. Urethra 10 is a duct leading from bladder 12, through prostate 14 and out orifice 16 of penis end 18. Benign tumorous tissue growth within prostate 14 around urethra 10 causes constriction 20 of urethra 10, which interrupts the flow of urine from neck 22 of bladder 12 to orifice 16. The tumorous tissue of prostate 14 which encroaches urethra 10 and causes constriction 20 can be effectively removed by heating and necrosing the encroaching tumorous tissue. Ideally, periurethral tumorous tissue of prostate 14 anterior and lateral to urethra 10 is heated and necrosed to avoid unnecessary and undesirous damage to urethra 10 and to adjacent healthy tissues, such as ejaculatory duct 24 and rectum 26. A selective heating of benign tumorous tissue of prostate 14 (transurethral thermal therapy) may be achieved by utilizing a microwave antenna-containing catheter such as is shown in U.S. Pat. No. 5,620,480 or U.S. Pat. No. 5,575,811, which have been incorporated herein by reference.

Figure 2:
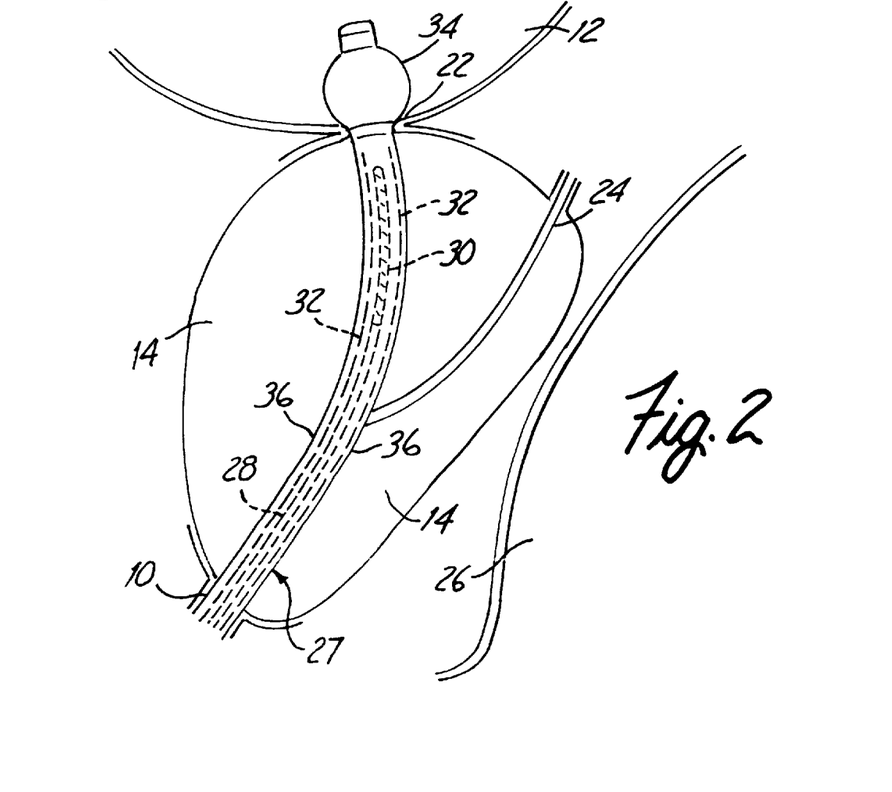
FIG. 2 is an enlarged view of the male pelvic region of FIG. 1 showing a urethral catheter positioned in the prostatic region.

FIG. 2 shows an enlarged view of the male pelvic region of FIG. 1 with a catheter 27 simplistically shown properly positioned within urethra 10. While the particular structure of catheter 27 may vary and a number of lumens may be provided therein, catheter 27 typically includes transmission line 28 connected to microwave antenna 30 for emitting microwave energy to prostate 14. Cooling fluid is circulated along paths 32 between microwave antenna 30 and the walls 36 of urethra 10, so as to conductively cool the tissue of urethra 10 when microwave antenna 30 is energized to radiate microwave energy to prostate 14. Catheter 27 may be secured within urethra 10 by retention balloon 34 located in bladder 12, for example. The temperature of the urethra may be detected by providing a temperature sensor on catheter 27 contacting urethral walls 36. In addition, the temperature of rectum 26 may be detected by inflating a balloon or providing another type of device in rectum 26 that includes a temperature sensor in contact with the rectal wall, such as is disclosed in U.S. Pat. No. 5,792,070 entitled RECTAL THERMOSENSING UNIT, which is hereby incorporated by reference.

Figure 3A:
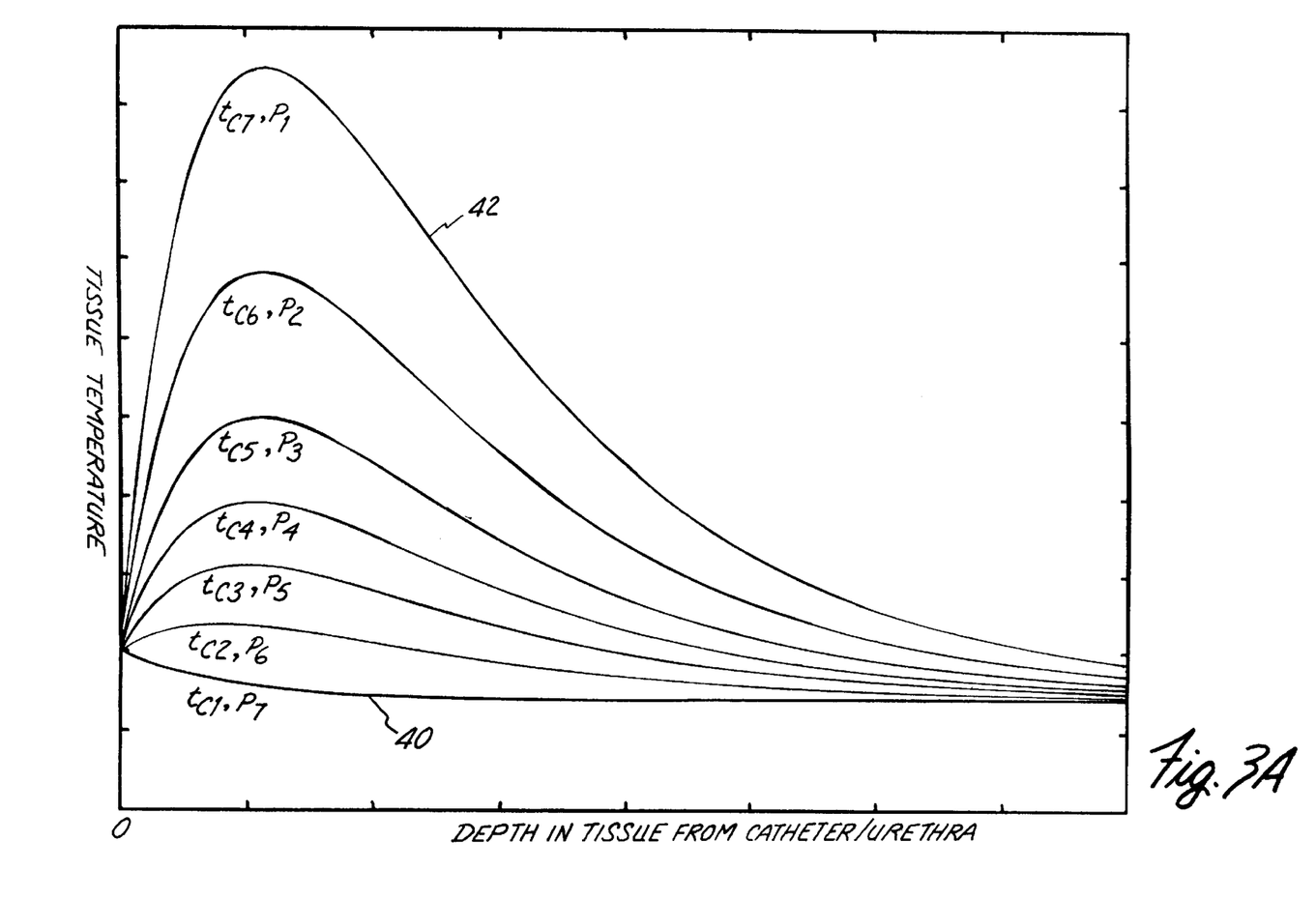
FIGS. 3A and 3B are graphs illustrating basic tissue temperature/depth curves at different power levels and coolant temperatures during thermal therapy.
Figure 3B:
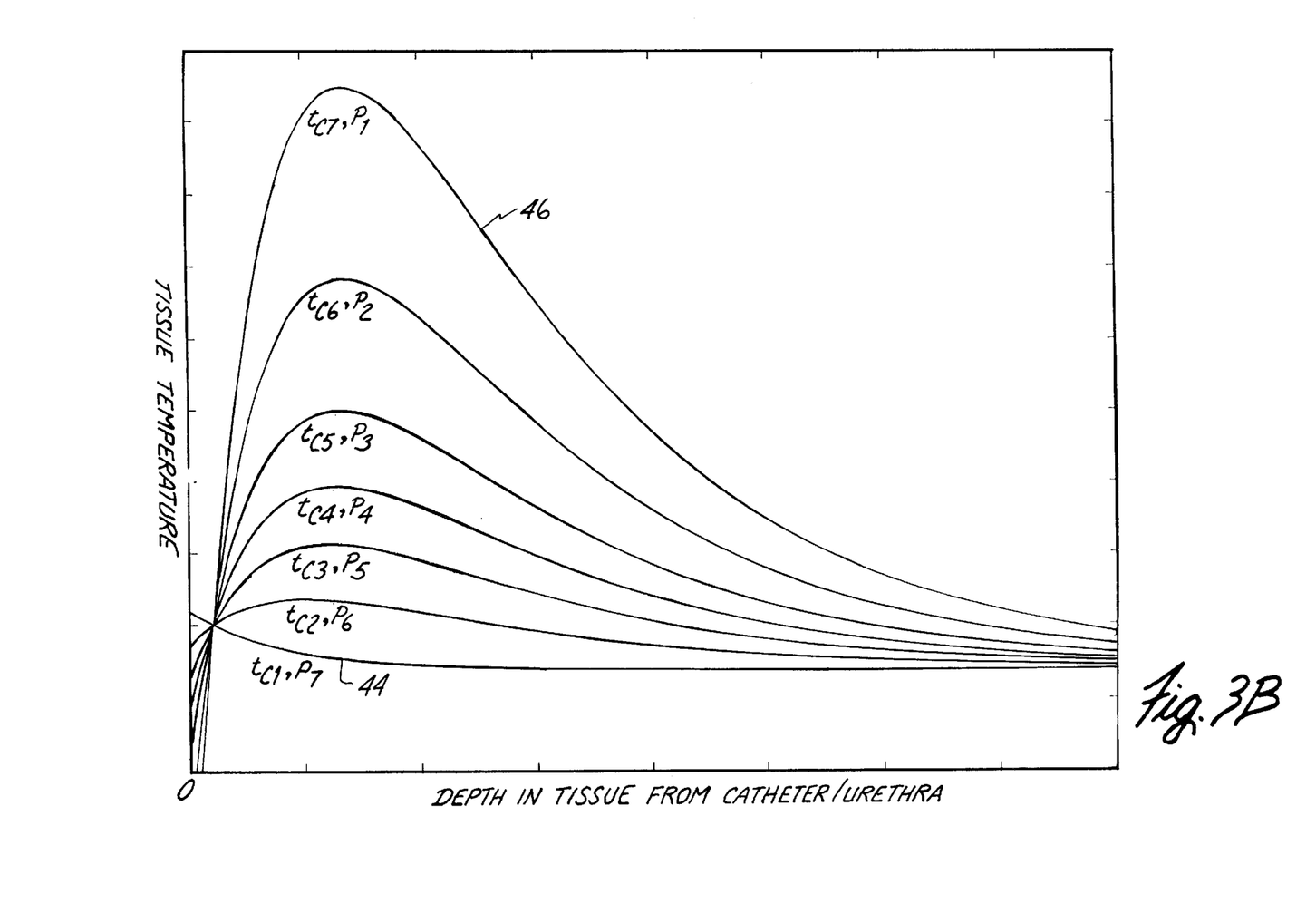

FIGS. 3A and 3B are graphs illustrating basic tissue temperature/depth curves at different power levels and coolant temperatures during thermal therapy, and demonstrating the basic principles of the present invention. Particularly, FIG. 3A illustrates tissue temperature/depth curves for a treatment session where catheter temperature is held at a predetermined value (such as 40° C.), and FIG. 3B illustrates tissue temperature/depth curves for a treatment session where a certain depth of tissue around the catheter is held at a predetermined value (such as 40° C.). The vertical axes of FIGS. 3A and 3B represent the temperature of tissue, and the horizontal axes represent the depth from the catheter/urethra of that tissue. Therefore, a depth of zero represents the urethral wall.

Each of the curves shown in FIG. 3A represents a different coolant temperature and microwave power condition, with the constant criteria for each curve being that the temperature of the catheter (at depth=0) is maintained at a steady-state temperature such as 40° C. Curve 40 represents a situation where microwave power is zero and coolant temperature is equal to the steady-state catheter temperature (e.g., 40° C.), curve 42 represents a situation where the microwave power is high and coolant temperature is at a minimum (such as 8° C., for illustrative purposes) and the curves between curve 40 and curve 42 represent situations where the microwave power is between zero and the high value, and the coolant temperature is between the steady-state catheter temperature (e.g., 40° C.) and the minimum coolant temperature (e.g., 8° C.). Each curve is labeled according to the relative coolant temperature ($t_c$) and power level (p), so that curve 40 represents the highest coolant temperature ($t_{c1}$) and the lowest power ($p_7$) and curve 42 represents the lowest coolant temperature ($t_{c7}$) and the highest power level ($p_1$), wherein each curve is predicated on the condition that catheter temperature is maintained at a steady-state temperature such as 40° C. The particular values of the minimum coolant temperature and corresponding power level depend on the structure and characteristics of the treatment catheter employed, and it should be understood that the exemplary values provided herein refer only to one particular catheter structure; other values are appropriate for different catheter structures, while still practicing the present invention. As can be seen from the curves shown in FIG. 3A, when the catheter temperature is maintained at a steady-state temperature such as 40° C., decreased coolant temperature results in deeper heating of tissue in the prostate due to the increased power level required to maintain the catheter at the steady-state temperature. This may result in a greater depth of necrosis caused by heating the tissue above a particular threshold temperature.

Each of the curves shown in FIG. 3B also represents a different coolant temperature and microwave power condition, with the constant criteria for each curve being that the temperature of tissue at a depth of interest, defining a zone of protection from the outer surface of the catheter to that tissue depth (such as 1 millimeter, for example), is maintained at a steady-state temperature such as 40° C. Curve 44 represents a situation where microwave power is slightly greater than zero and coolant temperature is equal to a temperature slightly greater than the steady-state tissue temperature (e.g., 40° C.), which is slightly different from the power and coolant temperature shown in curve 40 (FIG. 3A) where the catheter rather than a depth of tissue was maintained at a steady-state temperature such as 40° C. Curve 46 represents a situation where the microwave power is high and coolant temperature is at a minimum (such as 8° C., for illustrative purposes) and the curves between curve 44 and curve 46 represent situations where the microwave power is between zero and the high value, and the coolant temperature is between the steady-state tissue temperature (e.g., 40° C.) and the minimum coolant temperature (e.g., 8° C.). Each curve is labeled according to the relative coolant temperature ($t_c$) and power level (p), so that curve 44 represents the highest coolant temperature ($t_{c1}$) and the lowest power ($p_7$) and curve 46 represents the lowest coolant temperature ($t_{c7}$) and the highest power level ($p_1$), wherein each curve is predicated on the condition that tissue temperature is maintained at a steady-state temperature such as 40° C. The particular values of the minimum coolant temperature and corresponding power level depend on the structure and characteristics of the treatment catheter employed, and it should be understood that the exemplary values provided herein refer only to one particular catheter structure; other values are appropriate for different catheter structures, while still practicing the present invention. As can be seen from the curves shown in FIG. 3, when the tissue temperature at a depth of interest is maintained at a steady-state temperature such as 40° C., decreased coolant temperature results in deeper heating of tissue in the prostate due to the increased power level required to maintain the tissue at the steady-state temperature. This may result in a greater depth of necrosis caused by heating the prostate tissue above a particular threshold temperature.

In the thermal therapy curves depicted in FIGS. 3A and 3B, if coolant temperature is continually decreased and microwave power is correspondingly continually increased to maintain the catheter or tissue temperature at the steady-state temperature or at a set point temperature while initially ramping up the catheter/tissue temperature, temperatures at the depth of the rectum may become unacceptably high. In other words, high temperatures are achieved at too great of a depth from the catheter/urethra. Therefore, in a preferred method of controlling thermal therapy, rectal temperature is utilized as a parameter for controlling the coolant temperature (and the catheter/tissue temperature set point, temporarily) to enable optimal therapy without thermally damaging the tissue of the rectum.

Figure 4A:
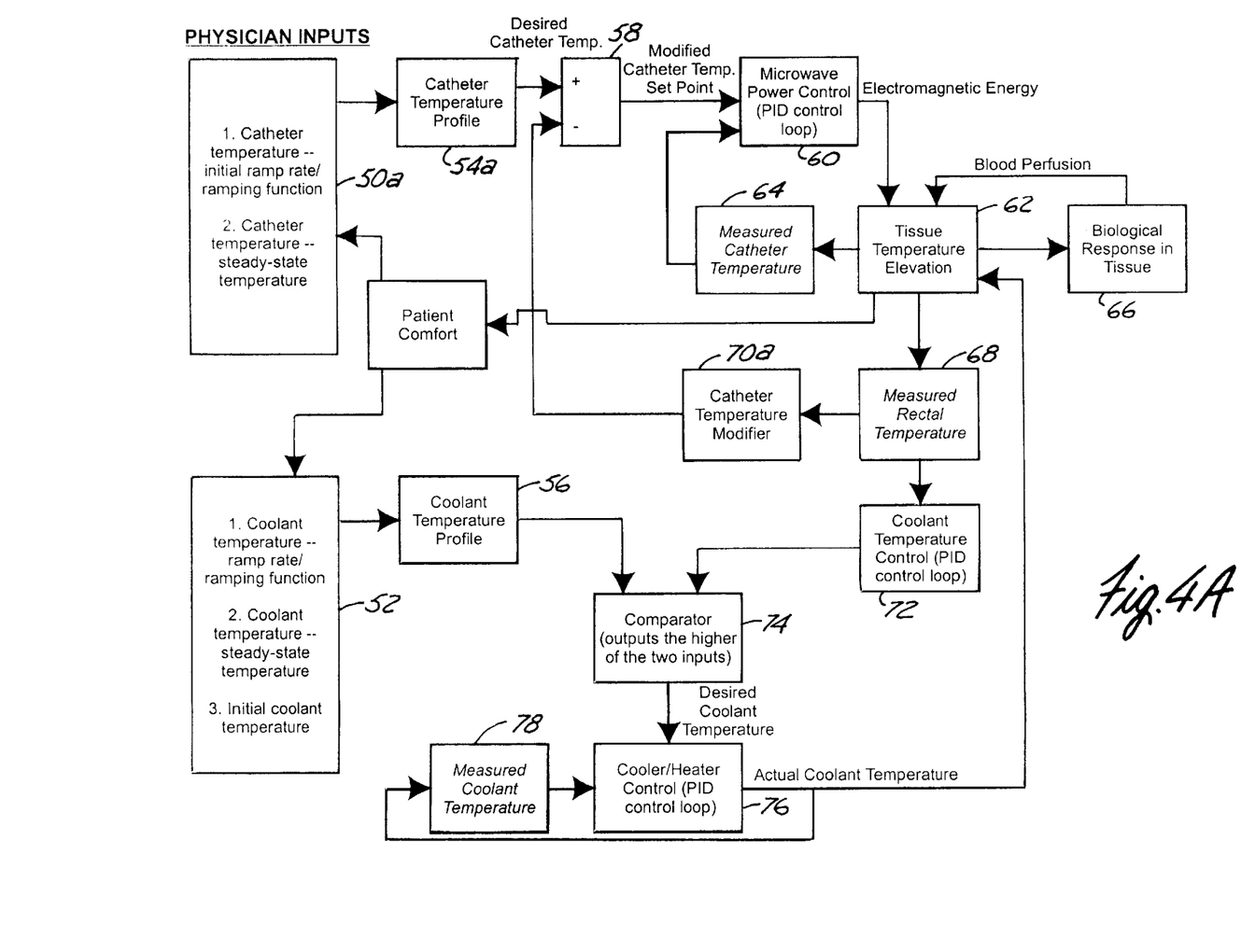
FIGS. 4A and 4B are block diagrams illustrating the thermal therapy control methods according to two embodiments of the present invention.

FIG. 4A is a block diagram illustrating a complete thermal therapy control method according to a first embodiment of the present invention, utilizing the principles and parameters discussed above with respect to FIG. 3A. To initialize the therapy, a physician enters inputs related to catheter temperature at block 50 and inputs related to coolant temperature at block 52. Specifically, a physician enters an initial ramp rate of catheter temperature (that is, how quickly and in what manner the catheter temperature is to increase from its initial temperature of approximately body temperature (37° C.) to its final, steady-state temperature) and a steady-state catheter temperature. In addition, the physician enters a coolant temperature ramp rate (that is, how quickly and in what manner the coolant temperature is to decrease from its initial temperature to a targeted final temperature), an initial coolant temperature and a steady-state coolant temperature. The catheter temperature ramp rate and the coolant temperature ramp rate may comprise a ramping function, such that catheter temperature and/or coolant temperature increases or decreases exponentially, linearly, or according to some other function that enhances the effectiveness of the therapy consistent with patient comfort concerns. The exact value and degree of physician contribution of these inputs will depend on experimental results of therapy in particular patients, and are set consistent with a desired patient comfort level. The actual format of physician input may also be simplified by an appropriate software program or other means, so that the physician enters only minimal data and the program calculates the therapy inputs from the data entered by the physician. The physician inputs are further explained graphically below with respect to FIGS. 5A and 5B.

From the catheter temperature inputs entered at block 50, a catheter temperature profile is established at block 54. The catheter temperature profile represents a desired characteristic of catheter temperature at a particular time in the thermal therapy session, which may of course be adjusted by other parameters such as rectal temperature and patient comfort during the course of the therapy, as noted below. From the coolant temperature inputs entered at block 52, a coolant temperature profile is established at block 56. The coolant temperature profile also represents a desired characteristic of coolant temperature at a particular time in the thermal therapy session, which again may be adjusted by other parameters such as rectal temperature and patient comfort during the course of the therapy, as noted below.

The catheter temperature profile signal is passed on to adder/subtractor 58, which passes a modified catheter temperature set point signal on to Microwave Power Control block 60, which in one preferred embodiment is implemented as a proportional/integral/differential (PID) control loop. PID control loops are algorithms known in the art for controlling a process to achieve a desired output level. The power delivered to the microwave antenna 30 (FIG. 2) energizes the antenna to radiate electromagnetic energy, resulting in elevation of prostate tissue as represented by block 62. Power delivered to the microwave antenna is continually adjusted to ensure that the catheter remains at the modified catheter temperature set point; therefore, Microwave Power Control block 60 is responsive to the measured catheter temperature at block 64 to adjust microwave power accordingly.

Elevation of prostate tissue temperature at block 62 causes a biological response in the tissue, which is represented by block 66. One response is increased blood perfusion in the tissue, which tends to conduct heat away from a particular portion of tissue and reduce the heating effect on the tissue. Also, when electromagnetic energy is delivered to elevate the temperature of prostate tissue, the temperature of the rectum may also be increased. Rectal temperatures are therefore monitored during thermal therapy to ensure that the rectum is not thermally damaged by excessively high temperatures; the measured rectal temperature is represented by block 68. If rectal temperature reaches a predetermined threshold, steps must be taken to reduce the temperature of the rectum so that it may be preserved. In an ideal situation, coolant temperature would be immediately increased (with microwave power correspondingly decreased to maintain catheter temperature at the desired set point) in response to high rectal temperatures. However, in actuality, it may not be possible to instantaneously change the temperature of the coolant. Therefore, to safely ensure preservation of the rectum, according to one preferred embodiment of the present invention, the catheter temperature is initially reduced in response to high rectal temperatures by a catheter temperature modifier represented at block 70. The catheter temperature modifier is subtracted by adder/subtractor 58 from the desired catheter temperature provided by the catheter temperature profile to yield a modified catheter temperature set point, which is input to Microwave Power Control block 60. By reducing the catheter temperature set point immediately, with all other parameters remaining the same, the microwave power will be reduced and tissue temperatures will immediately decrease. For increasingly higher rectal temperatures, the catheter temperature set point is decreased by a greater amount. In addition, a Coolant Temperature Control block 72 implements a PID control loop, for example, to determine an increased temperature of the coolant. Comparator block 74 outputs the higher of the coolant temperature provided by the coolant temperature profile at block 56 and the coolant temperature provided by Coolant Temperature Control block 72. In other words, the desired coolant temperature is determined by the coolant temperature profile at block 56 unless an excessively high rectal temperature causes a higher coolant temperature to be determined by Coolant Temperature Control block 72. The desired coolant temperature is input to Cooler/Heater Control block 76 along with the measured coolant temperature at block 78, and Cooler/Heater Control block 76 implements a PID control loop, for example, to adjust coolant temperature and stabilize the coolant at the appropriate temperature. The actual coolant temperature affects the temperature of the catheter and temperature to which prostate tissue and the rectum are elevated, which is represented by the line from Cooler/Heater Control block 76 to the tissue temperature elevation shown at block 62. Finally, as the rectal temperature returns to a value below the threshold, the catheter temperature modifier is reduced to zero, and the catheter temperature returns to the value provided by the catheter temperature profile at block 54, with the system stabilizing at the higher coolant temperature. By implementing this control method, rectal temperatures (and prostate tissue temperatures) reach the highest attainable level without exceeding a threshold rectal temperature, while simultaneously maintaining the catheter temperature set point at the maximum desired value consistent with patient comfort. It is somewhat counter-intuitive that coolant temperature should be increased in response to excessively high temperatures in the rectum, but it is nonetheless true where the catheter temperature is constrained to a predetermined steady-state value, since an increase in coolant temperature effectively forces a reduction in power provided to the microwave antenna to maintain the catheter at the steady-state value. The method of the present invention therefore enhances the effectiveness and reduces the necessary treatment time of the therapy.

The thermal therapy controlled by the method of the present invention must take into account the comfort level of the patient at various phases of the therapy. For example, the catheter temperature ramp rate or ramping function or the steady-state catheter temperature may potentially drive changes in power that may result in discomfort for the patient. Similarly, the coolant temperature ramp rate or ramping function or other parameters may also result in power level changes that could potentially cause some patient discomfort. As the thermal therapy session progresses, a physician may adjust the therapy at any time in response to an indication of patient discomfort, represented by block 79. Patient discomfort may potentially occur as a result of high absolute temperatures, or also as a result of high rates of change of temperatures, and therapy therefore is adjustable to change parameters related to both of these factors. The therapy parameter changes implemented by the physician (at blocks 50 and 52) are integrated into the therapy control method of the present invention to reduce or eliminate the discomfort of the patient.

Figure 4B:
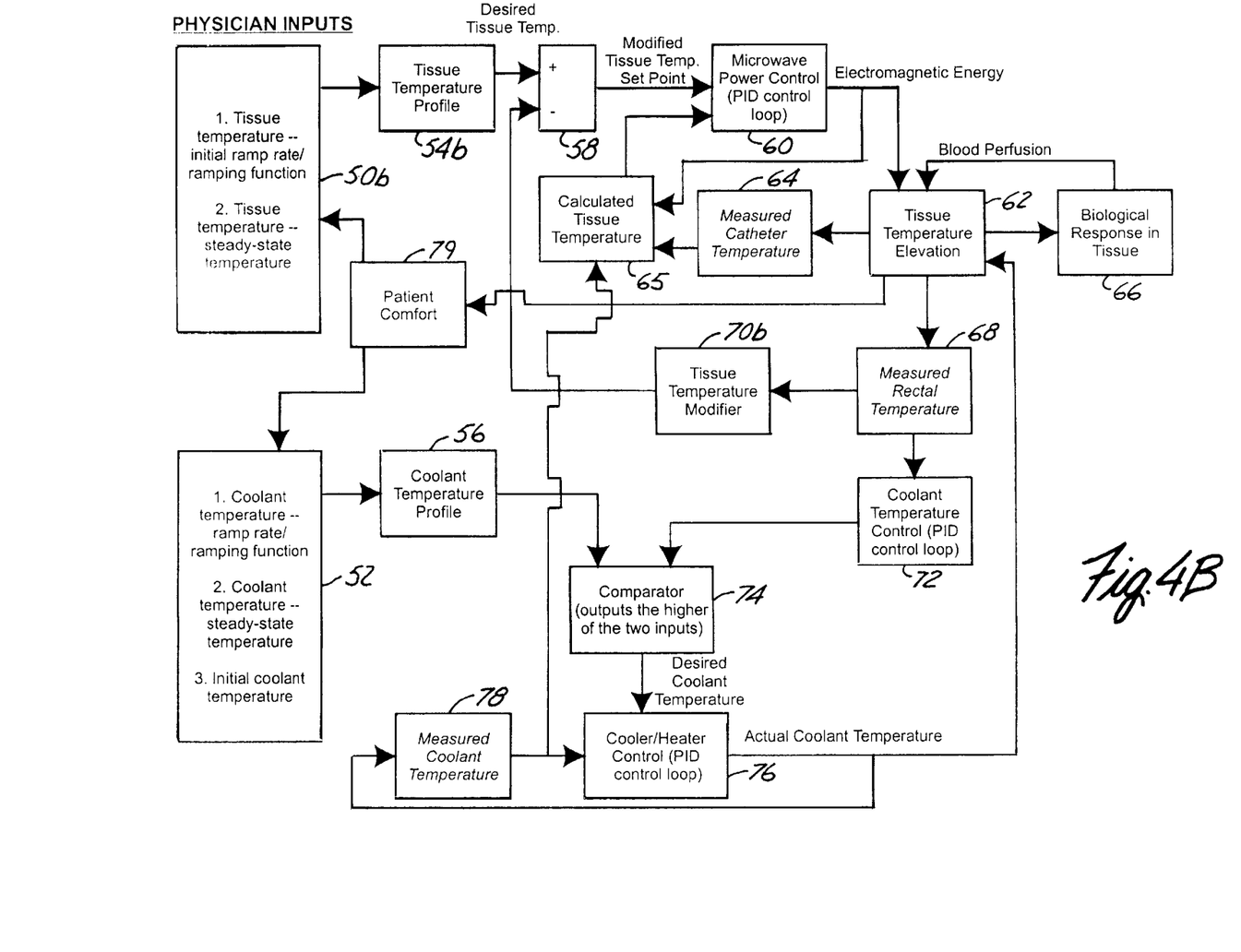

FIG. 4B is a block diagram illustrating a complete thermal therapy control method according to a second embodiment of the present invention, utilizing the principles and parameters discussed above with respect to FIG. 3B. The majority of the method shown in FIG. 4B is identical to that shown in FIG. 4A, with one principal modification. Instead of utilizing a catheter temperature set point as shown in FIG. 4A, the modified method shown in FIG. 4B is concerned with a tissue temperature set point (that is, the temperature in tissue at some depth of interest from the catheter/urethra, defining a tissue protection zone). Therefore, to initialize the therapy, a physician enters an initial tissue temperature ramp rate/ramping function and a steady-state tissue temperature at block 50*b*, in a manner substantially similar to that described with respect to block 50*a* of FIG. 4A. From the tissue temperature inputs entered at block 50*b*, a tissue temperature profile is established at block 54*b*, which represents a desired characteristic of tissue temperature at a particular time in the thermal therapy session, which may of course be adjusted by other parameters such as rectal temperature and patient comfort during the course of the therapy, as noted below.

The tissue temperature profile signal is passed on to adder/subtractor 58, which passes a modified tissue temperature set point signal on to Microwave Power Control block 60, which is implemented as described above with respect to FIG. 4A. The power delivered to microwave antenna 30 (FIG. 2) energizes the antenna to radiate electromagnetic energy, resulting in elevation of prostate tissue as represented by block 62. Power delivered to the microwave antenna is continually adjusted to ensure that tissue at the depth of interest remains at the modified tissue temperature set point. In order to do so, Microwave Power Control block 60 must be responsive to tissue temperature. However, tissue temperature at a depth from the catheter/urethra typically cannot be measured directly without penetrating the urethra. Therefore, in one embodiment of the present invention, catheter temperature is measured at block 64, and tissue temperature is calculated at block 65 based on the measured catheter temperature (block 64), the microwave power level (block 60) and the measured coolant temperature (block 78). Microwave Power Control block 60 is therefore responsive to the calculated tissue temperature at block 65 to adjust microwave power accordingly. In an alternative embodiment, a temperature sensor may be positioned in the tissue by penetrating the urethra, or some other temperature sensing system for directly measuring tissue temperature may be implemented, in which case the measured tissue temperature would replace measured catheter temperature at block 64 of FIG. 4A, and there would be no need to calculate tissue temperature.

Rectal temperatures are also monitored during thermal therapy to ensure that the rectum is not thermally damaged by excessively high temperatures; the measured rectal temperature is represented by block 68. If rectal temperature reaches a predetermined threshold, steps must be taken to reduce the temperature of the rectum so that it may be preserved. As described above with respect to FIG. 4A, since coolant temperature may not be able to be instantaneously increased, the temperature set point is initially decreased to force microwave power to be immediately reduced. This tissue temperature set point is reduced by the tissue temperature modifier represented at block 70*b*, which is subtracted by adder/subtractor 58 from the desired tissue temperature to yield a modified tissue temperature set point input to Microwave Power Control block 60. As also described above with respect to FIG. 4A, after coolant temperature is increased and rectal temperature is returning to a value below the threshold, the tissue temperature modifier is reduced to zero, and the tissue temperature returns to the value provided by the tissue temperature profile at block 54*b*, with the system stabilizing at the higher coolant temperature.

Figure 5A:
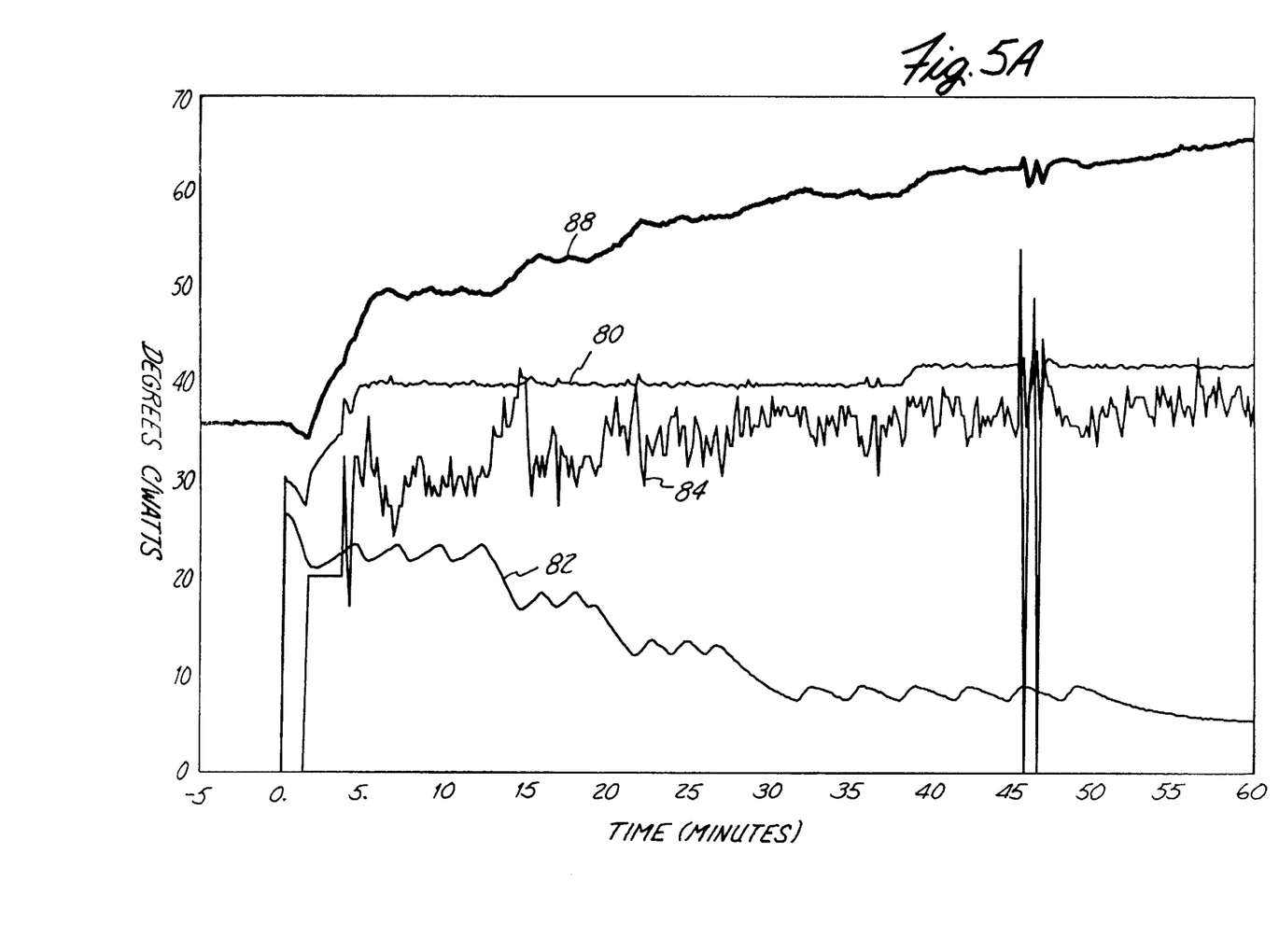
FIG. 5A is a graph illustrating temperatures achieved during a thermal therapy treatment session according to one variation of the control method of the present invention.

FIG. 5A is a graph illustrating measured temperatures achieved during an actual thermal therapy treatment session in a clinical trial according to one variation of the control method of the present invention. In the clinical trial, anesthesia was used to ensure that the patients remained comfortable, so the patient comfort adaptability of the present invention was not utilized in the trial. Curve 80 represents the temperature of the catheter inserted into the urethra of the patient. Curve 82 represents the temperature of the coolant circulated between the antenna in the catheter and the urethral wall; the small oscillations in curve 82 are due to the heating/cooling system utilized in the trial. Curve 84 represents the microwave power level delivered to the antenna. Curve 88 represents the temperature of tissue at a depth of approximately 0.5 cm in the prostate surrounding the urethra.

Initially, power (curve 84) was ramped up quickly to raise the temperature of the catheter (curve 80) to approximately 40° C. (the catheter temperature set point), with coolant temperature (curve 82) at an initial value of approximately 22° C. These characteristics correspond to the catheter temperature ramp rate and the initial coolant temperature set by the physician at blocks 50*a* and 52 (FIG. 4A). The ramp rate and ramping function may vary as described above; the clinical trial shown in FIG. 5A utilized a unit step function, which increased catheter temperature to the steady-state value as quickly as the system capabilities permitted. Coolant temperature was then reduced in step-wise increments, while the microwave power level was increased in turn to maintain the catheter temperature at the steady-state temperature such as 40° C. (set by the physician in block 50*a*, FIG. 4A). The step-wise decrease in coolant temperature was set by the physician as the coolant temperature ramp rate (block 52, FIG. 4A); again, the ramp rate and ramping function can vary as described above. As a result, the temperature of prostate tissue (curve 88) increased in a corresponding step-wise manner to the coolant temperature decrease. Coolant temperature finally reached a steady-state temperature, which again had been set by the physician at block 52, FIG. 4A. Also, throughout the therapy, rectal temperature was monitored to ensure that temperatures do not exceed a predetermined threshold, to prevent thermal damage to the rectum; no excessively high rectal temperatures were detected.

At a treatment time between 30 and 40 minutes, the catheter temperature set point (curve 80) was increased from 40° C. to 42° C. for experimental purposes. As expected, the increase in steady-state catheter temperature resulted in a corresponding increase in power (curve 84) and tissue temperature (curve 88), while the coolant temperature (curve 82) was kept constant.

Microwave power curve 84, catheter temperature curve 80 and tissue temperature curve 88 experience some oscillation at a treatment time between 40 and 50 minutes. These oscillations were due to a bladder spasm experienced by the patient at this time, which may occur from time to time during a thermal therapy treatment session. During the bladder spasm, although catheter temperature oscillated briefly, the control method of the present invention caused it to remain at a level approximately equal to or below the catheter temperature set point, and catheter temperature returned to the steady-state temperature automatically and stabilized with no outside intervention when the bladder spasm ceased.

Figure 5B:
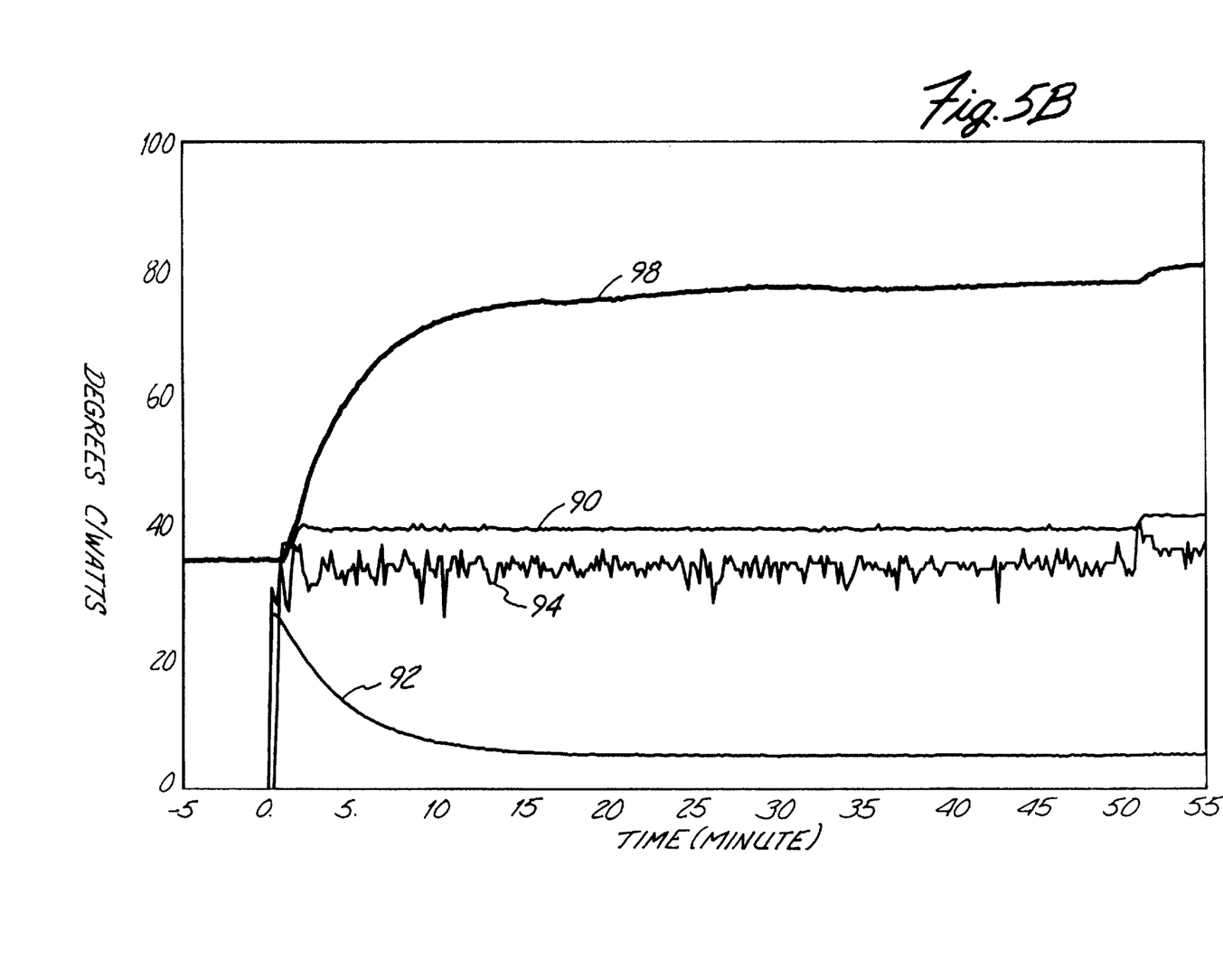
FIG. 5B is a graph illustrating temperatures achieved during a thermal therapy treatment session according to a second variation of the control method of the present invention.

FIG. 5B is a graph illustrating measured temperatures achieved during an actual thermal therapy treatment session in a clinical trial according to a second variation of the control method of the present invention. In the clinical trial, anesthesia was used to ensure that the patients remained comfortable, so the patient comfort adaptability of the present invention was not utilized in the trial. Curve 90 represents the temperature of the catheter inserted into the urethra of the patient. Curve 92 represents the temperature of the coolant circulated between the antenna in the catheter and the urethral wall. Curve 94 represents the microwave power level delivered to the antenna. Curve 98 represents the temperature of tissue at a depth of approximately 0.5 cm in the prostate surrounding the urethra.

Initially, power (curve 94) was ramped up quickly to raise the temperature of the catheter (curve 90) to approximately 40° C. (the catheter temperature set point), with coolant temperature (curve 92) at an initial value of approximately 28° C. These characteristics correspond to the catheter temperature ramp rate and the initial coolant temperature set by the physician at blocks 50a and 52 (FIG. 4A). The ramp rate and ramping function may vary as described above; the clinical trial shown in FIG. 5B utilized a unit step function, which increased catheter temperature to the steady-state value as quickly as the system capabilities permitted. Coolant temperature was then reduced quickly, while the microwave power level was increased in turn to maintain the catheter temperature at the steady-state temperature such as 40° C. (set by the physician in block 50a, FIG. 4A). The decrease in coolant temperature was set by the physician as the coolant temperature ramp rate (block 52, FIG. 4A); the function utilized was a unit step function causing coolant to decrease in temperature as quickly as the heating/cooling system would allow, but again, the ramp rate and ramping function can vary as described above. As a result, the temperature of prostate tissue (curve 98) increased in a manner corresponding to the coolant temperature decrease. Coolant temperature finally reached a steady-state temperature, which again, had been set by the physician at block 52, FIG. 4A. Also, throughout the therapy, rectal temperature was monitored to ensure that temperatures do not exceed a predetermined threshold, to prevent thermal damage to the rectum; no excessively high rectal temperatures were detected. As can be seen in FIG. 5B, tissue temperatures exceeding about 90% of the peak tissue temperature were obtained within about 10 minutes.

It should be understood that the particular temperatures set and observed in the clinical trials illustrated by FIGS. 5A and 5B are exemplary, and the particular temperatures chosen and observed in practicing the present invention will vary depending on the patient's comfort level, the particular catheter structure utilized, and other factors.

The thermal therapy control method of the present invention is significantly different from prior art control methods, in that the therapy is driven by controlling coolant temperature and making automatic corresponding adjustments to microwave power to maintain catheter or tissue temperature at a particular set point. In the absence of limiting parameters, coolant temperature is preferably as low as possible, so that microwave power is forced to correspondingly increase to maintain catheter temperature constant and tissue is therefore heated to maximum temperatures. Rectal temperature is one factor that limits the therapy, since the rectum must be preserved below a threshold temperature to avoid thermal damage. The control method of the present invention allows the thermal therapy system to be optimally operated, with rectal temperatures as high as possible without thermally damaging the rectum and catheter temperatures maintained at a predetermined steady-state operating temperature. As a result, a precise depth of tissue necrosis is achievable with no physician intervention to control the therapy. Therapy times are also minimized, since the control method of the present invention allows tissue temperatures to reach 90% of their maximum value within about 10 minutes, if tolerable by the patient, which is a significant improvement over the prior art.

The thermal therapy control method of the present invention has been described primarily as it applies to treatment of a prostate from a urethra. However, the principles and methods of the present invention are likewise applicable to thermally treating other regions of tissue from adjacent body cavities. Preservation of adjacent organs may also be applicable, in a manner similar to the preservation of the rectum described above with respect to one preferred embodiment of the invention.

Although the present invention has been described with reference to preferred embodiments, workers skilled in the art will recognize that changes may be made in form and detail without departing from the spirit and scope of the invention.

What is claimed is:

1. A thermal therapy method comprising:

inserting an applicator including an energy-emitting device into a body cavity adjacent a targeted tissue region;

energizing the energy-emitting device;

circulating coolant between the energy-emitting device and a wall of the body cavity;

controlling a temperature of the coolant circulated between the energy-emitting device and the wall of the body cavity on a continual basis based on therapy parameters, wherein the step of controlling coolant temperature based on therapy parameters comprises monitoring a temperature of an adjacent body organ; and maintaining the applicator at a temperature corresponding to a predetermined applicator temperature profile by adjusting a power level provided to the energy-emitting device, wherein coolant temperature is increased in response to a body organ temperature greater than a predetermined threshold, thereby forcing a reduction in the power level provided to the energy-emitting device to maintain the applicator at the temperature corresponding to the predetermined applicator temperature profile.

2. The thermal therapy method of claim 1, further comprising the step of temporarily decreasing the applicator temperature from the predetermined applicator temperature profile upon detecting a body organ temperature greater than the predetermined threshold.

3. The thermal therapy method of claim 1, wherein coolant temperature is initially preset to a minimum value.

4. The thermal therapy method of claim 1, wherein the body cavity is a urethra and the targeted tissue region is prostate tissue, and wherein the step of controlling coolant temperature based on therapy parameters comprises monitoring rectal temperature and adjusting coolant temperature in response to a predetermined rectal temperature profile, thereby forcing a corresponding adjustment of the power level provided to the energy-emitting device to maintain the applicator at the temperature corresponding to the predetermined applicator temperature profile.

5. The thermal therapy method of claim 4, further comprising the step of temporarily adjusting the applicator temperature from the predetermined applicator temperature profile upon detecting the predetermined rectal temperature profile.

6. A thermal therapy method comprising:
    inserting an applicator including an energy-emitting device into a body cavity adjacent a targeted tissue region;
    energizing the energy-emitting device;
    circulating coolant between the energy-emitting device and a wall of the body cavity;
    controlling a temperature of the coolant circulated between the energy-emitting device and the wall of the body cavity on a continual basis based on therapy parameters, wherein the step of controlling coolant temperature based on therapy parameters comprises monitoring a temperature of an adjacent body organ; and
    maintaining the applicator at a temperature corresponding to a predetermined applicator temperature profile by adjusting a power level provided to the energy-emitting device, wherein coolant temperature is continually adjusted to maintain the temperature of the adjacent body organ at a predetermined value, thereby forcing corresponding adjustment of the power level provided to the energy-emitting device to maintain the applicator at the temperature corresponding to the predetermined applicator temperature profile.

7. The thermal therapy method of claim 6, further comprising the step of temporarily adjusting the applicator temperature from the predetermined applicator temperature profile upon detecting a predetermined body organ temperature profile.

8. A thermal therapy method comprising:
    inserting an applicator including an energy-emitting device into a body cavity adjacent a targeted tissue region, wherein the body cavity is a urethra and the targeted tissue region is prostate tissue;
    energizing the energy-emitting device;
    circulating coolant between the energy-emitting device and a wall of the body cavity;
    controlling a temperature of the coolant circulated between the energy-emitting device and the wall of the body cavity on a continual basis based on therapy parameters; and
    maintaining the applicator at a temperature corresponding to a predetermined applicator temperature profile by adjusting a power level provided to the energy-emitting device, wherein the step of controlling coolant temperature based on therapy parameters comprises monitoring rectal temperature and increasing coolant temperature in response to a rectal temperature greater than a predetermined threshold, thereby forcing a reduction in the power level provided to the energy-emitting device to maintain the applicator at the temperature corresponding to the predetermined applicator temperature profile.

9. The thermal therapy method of claim 8, further comprising the step of temporarily decreasing the applicator temperature from the predetermined applicator temperature profile upon detecting a rectal temperature greater than the predetermined threshold.

10. A method of treating a prostate with heat via a urethra comprising:
    inserting a microwave antenna-containing applicator into the urethra adjacent the prostate;
    inserting a rectal temperature sensing probe into a rectum;
    providing power to the microwave antenna while circulating coolant between the microwave antenna and a wall of the urethra;
    adjusting a temperature of the coolant to a steady-state coolant temperature;
    maintaining the applicator at a temperature corresponding to a predetermined applicator temperature profile by continually adjusting the power provided to the microwave antenna; and
    monitoring rectal temperature with the rectal temperature sensing probe and, upon sensing a predetermined rectal temperature profile, increasing the coolant temperature and thereby forcing a reduction in power provided to the microwave antenna to maintain the applicator at the temperature corresponding to the predetermined applicator temperature profile.

11. The method of claim 10, further comprising the step of temporarily decreasing the applicator temperature from the predetermined applicator temperature profile upon detecting the predetermined rectal temperature profile.

12. The method of claim 10, wherein the predetermined applicator temperature profile and the steady-state coolant temperature are input by a physician.

13. The method of claim 10, wherein the predetermined applicator temperature profile is a constant temperature of about 40° C.

14. The method of claim 10, wherein a catheter temperature ramp rate, an initial coolant temperature and a coolant temperature ramp rate are input by a physician.

15. The method of claim 10, wherein the predetermined applicator temperature profile, the steady-state coolant temperature, a catheter temperature ramp rate, an initial coolant temperature and a coolant temperature ramp rate are adjustable in response to patient comfort indicators.

16. A thermal therapy method comprising:
    inserting an applicator including an energy-emitting device into a body cavity adjacent a targeted tissue region;
    energizing the energy-emitting device;
    circulating coolant between the energy-emitting device and a wall of the body cavity;

controlling a temperature of the coolant circulated between the energy-emitting device and the wall of the body cavity on a continual basis based on therapy parameters, wherein the step of controlling coolant temperature based on therapy parameters comprises monitoring a temperature of an adjacent body organ; and maintaining selected tissue at a predetermined depth from the wall of the body cavity at a temperature corresponding to a predetermined tissue temperature profile by adjusting a power level provided to the energy-emitting device in coordination with the coolant temperature, wherein coolant temperature is increased in response to a body organ temperature greater than a predetermined threshold, thereby forcing a reduction in the power level provided to the energy-emitting device to maintain the selected tissue at the temperature corresponding to the predetermined tissue temperature profile.

17. The thermal therapy method of claim 16, further comprising the step of temporarily decreasing the selected tissue temperature from the predetermined tissue temperature profile upon detecting a body organ temperature greater than the predetermined threshold.

18. A thermal therapy method comprising:

inserting an applicator including an energy-emitting device into a body cavity adjacent a targeted tissue region, wherein the body cavity is a urethra and the targeted tissue region is prostate tissue;

energizing the energy-emitting device;

circulating coolant between the energy-emitting device and a wall of the body cavity;

controlling a temperature of the coolant circulated between the energy-emitting device and the wall of the body cavity on a continual basis based on therapy parameters; and maintaining selected tissue at a predetermined depth from the wall of the body cavity at a temperature corresponding to a predetermined tissue temperature profile by adjusting a power level provided to the energy-emitting device in coordination with the coolant temperature, and wherein the step of controlling coolant temperature based on therapy parameters comprises monitoring rectal temperature and increasing coolant temperature in response to a rectal temperature greater than a predetermined threshold, thereby forcing a reduction in the power level provided to the energy-emitting device to maintain the selected tissue at the temperature corresponding to the predetermined tissue temperature profile.

19. The thermal therapy method of claim 18, further comprising the step of temporarily decreasing the selected tissue temperature from the predetermined tissue temperature profile upon detecting a rectal temperature greater than the predetermined threshold.

20. A method of treating a prostate with heat via a urethra comprising:

inserting a microwave antenna-containing applicator into the urethra adjacent the prostate;

inserting a rectal temperature sensing probe into a rectum;

providing power to the microwave antenna while circulating coolant between the microwave antenna and a wall of the urethra;

decreasing a temperature of the coolant to a steady-state coolant temperature;

maintaining selected tissue at a predetermined depth from the wall of the urethra at a temperature corresponding to a predetermined tissue temperature profile by continually adjusting the power provided to the microwave antenna in coordination with the coolant temperature; and monitoring rectal temperature with the rectal temperature sensing probe and, upon sensing a predetermined rectal temperature profile, increasing the coolant temperature so as to force a reduction in power provided to the microwave antenna to maintain the selected tissue at the temperature corresponding to the predetermined tissue temperature profile.

21. The method of claim 20, wherein the predetermined tissue temperature profile of the selected tissue and the steady-state coolant temperature are input by a physician.

22. The method of claim 20, wherein the predetermined tissue temperature profile is a constant temperature of about 40° C.

23. The method of claim 20, wherein a catheter temperature ramp rate, an initial coolant temperature and a coolant temperature ramp rate are input by a physician.

24. The method of claim 20, wherein the predetermined tissue temperature profile, the steady-state coolant temperature, a catheter temperature ramp rate, an initial coolant temperature and a coolant temperature ramp rate are adjustable in response to patient comfort indicators.

25. The method of claim 20, further comprising the step of temporarily decreasing the tissue temperature from the predetermined tissue temperature profile upon detecting the predetermined rectal temperature profile.

* * * * *